(12) United States Patent
Martens et al.

(10) Patent No.: US 9,248,301 B2
(45) Date of Patent: Feb. 2, 2016

(54) SYSTEM AND METHOD FOR COMMUNICATING INFORMATION BETWEEN IMPLANTABLE DEVICES

(75) Inventors: Hubert Cécile François Martens, Eindhoven (NL); Franciscus Paulus Maria Budzelaar, Eindhoven (NL); Jeroen Jacob Arnold Tol, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 273 days.

(21) Appl. No.: 13/054,857

(22) PCT Filed: Jul. 22, 2009

(86) PCT No.: PCT/IB2009/053165
§ 371 (c)(1),
(2), (4) Date: Mar. 21, 2011

(87) PCT Pub. No.: WO2010/013170
PCT Pub. Date: Feb. 4, 2010

(65) Prior Publication Data
US 2011/0184492 A1 Jul. 28, 2011

(30) Foreign Application Priority Data
Jul. 29, 2008 (EP) .................................. 08161331

(51) Int. Cl.
*A61N 1/362* (2006.01)
*A61N 1/372* (2006.01)
(52) U.S. Cl.
CPC ............ *A61N 1/37288* (2013.01); *A61N 1/362* (2013.01); *A61N 1/37252* (2013.01)
(58) Field of Classification Search
CPC ........................... A61N 1/362; A61N 1/37288

USPC ........................................................... 607/60
See application file for complete search history.

(56) References Cited

U.S. PATENT DOCUMENTS 5,113,859 A * 5/1992 Funke .............................. 607/4
5,649,970 A 7/1997 Loeb et al.
(Continued)

FOREIGN PATENT DOCUMENTS

WO 2007028035 A2 3/2007

OTHER PUBLICATIONS

Sun et al: "Biological Resources Within the Human Body Can Be Used to Operate Neural Implants"; 2005 First International Conference on Neural Interface and Control Proceedings; May 2005, IEEE, pp. 6-9.

(Continued)

*Primary Examiner* — William Levicky

(57) ABSTRACT

A system for communicating information between at least two medical devices implanted within the body of a subject using volume conduction of electrical signals as a means of communication and wherein one of the implanted medical devices is configured to provide electrical stimulation to the tissue is disclosed. The system comprises a first implant device having at least two transmit electrodes configured to transmit electrical stimulation pulses, wherein one of the electrodes may be a common return electrode, an encoding means configured to employ a channel as a transmitter transmission medium for stimulation pulses and encoding the information into the stimulation pulses, a second implant device having at least two receive electrodes configured to receive the transmitted stimulation pulses with encoded information, and a decoding means configured to decode the information encoded into the stimulation pulses. The disclosed system provides reliable and efficient communication between implantable devices.

7 Claims, 8 Drawing Sheets

(56) References Cited

U.S. PATENT DOCUMENTS

| | | | |
|---|---|---|---|
| 5,899,928 A * | 5/1999 | Sholder et al. | 607/27 |
| 7,346,391 B1 * | 3/2008 | Osorio et al. | 607/2 |
| 7,630,767 B1 * | 12/2009 | Poore et al. | 607/32 |
| 2004/0199222 A1 | 10/2004 | Sun et al. | |
| 2005/0197680 A1 * | 9/2005 | DelMain et al. | 607/60 |
| 2006/0136001 A1 * | 6/2006 | Ortega et al. | 607/9 |
| 2007/0088397 A1 * | 4/2007 | Jacobson | 607/9 |
| 2007/0088405 A1 | 4/2007 | Jacobson | |
| 2007/0228273 A1 | 10/2007 | Sun et al. | |
| 2008/0306359 A1 * | 12/2008 | Zdeblick et al. | 600/302 |

OTHER PUBLICATIONS

Sun et al: "Data Communication Between Brain Implants and Computer"; IEEE Transactions on Neural Systems and Rehabilitation Engineering, Jun. 2003, vol. 11, No. 2, pp. 189-192.

* cited by examiner

SYSTEM AND METHOD FOR COMMUNICATING INFORMATION BETWEEN IMPLANTABLE DEVICES

FIELD OF THE INVENTION

The present subject matter relates to a system for communicating information between implantable devices and more specifically to a system for communicating information between implantable devices using volume conduction of electrical signals.

BACKGROUND OF THE INVENTION

Patent document WO2007/028035 discloses a system for communicating information within the body of an animal. The system comprises a first device comprising a transmitter configured to transmit a signal via a quasi electrostatic coupling to the body of the patient and a second device comprising a receiver configured to receive the transmitted signal via a quasi electrostatic coupling to the body of the patient. The data is transmitted using a carrier signal having a carrier frequency typically in the range of about 10-100 KHz. Data is encoded using known modulation techniques such as amplitude modulation, frequency modulation or phase modulation of the carrier signal.

The solution disclosed in WO2007/028035 may not be well suited for electro-stimulation devices as the stimuli can contaminate the data signals. This can result in unreliable data transmission. Further, the data signal generation may require additional electronics. Dedicated signal generation circuits may be needed to generate the data carrying signal and dedicated transmit/receive electrode pairs may be needed to transmit and receive the data signals.

Hence, it would be advantageous to have an improved system that can reliably communicate information between two medical devices implanted within the body of a subject.

SUMMARY OF THE INVENTION

Accordingly, the present subject matter preferably seeks to mitigate, alleviate or eliminate one or more of the above mentioned disadvantages singly or in combination. In particular, it may be seen as an object of the present subject matter to provide an improved system for communicating information between two or more medical devices implanted within the body of a subject.

This object and several other objects are obtained in a first aspect of the present subject matter by providing a system for communicating information between at least two medical devices implanted within the body of a subject using volume conduction of electrical signals as a means of communication, the system comprising:

a first implant device having at least two transmit electrodes configured to transmit stimulation pulses, wherein one of the electrodes may be a common return electrode;

an encoding means configured to employ a channel as a transmission medium for stimulation pulses and encode the information into the stimulation pulses;

a second implant device having at least two receive electrodes configured to receive the transmitted stimulation pulses with encoded information; and a decoding means configured to decode the information encoded into the stimulation pulses.

The disclosed solution is based on the insight that the channel that is used for delivery of stimuli to the body of the subject can be used as well to transmit the information between the implants. The disclosed system can overcome the problem of data contamination. The disclosed system provides several means to encode the information. The information may be carried by the timing or shapes of pulses themselves or be interlaced in between stimulation pulses. For instance information may be encoded in the timing of the stimulation pulses, or information may be encoded in electrical signals (i.e. pulses or oscillatory waveforms) that are transmitted in the otherwise silent periods between subsequent electrical stimulation pulses. Hence, the problem of the data signal getting contaminated by the presence of electrical stimulation can be circumvented.

Further, by making use of the stimulation pulse signals, the same circuitry and electrodes present in the first implant device for therapeutic use can be re-used for transmitting the information.

The information to be encoded could be a range of data such as implant device settings, implant device status and recorded physiological signals. The word encoding here refers to obtaining a representation of the data (e.g. a list of numbers) that is suitable for transmission (e.g. a bit stream).

In an embodiment, the encoding means is configured to use the timing and/or the shape of the therapeutic stimulation pulses as a means to encode the information. This embodiment can effectively make use of the therapeutic pulses that are already generated.

As an illustrative example, nerves partially loosing their function as a result of disease or trauma are generally stimulated using electrical stimulation pulses. A neurostimulator implant can be used for such purpose. The information can be encoded using such electrical stimulation pulses.

In a further embodiment, the encoding means is configured to use non-therapeutic electrical signals (i.e. pulses) as a means to encode the information. Implant devices that are not configured to provide electrical stimulation can use non-therapeutic signals to encode the information. Also, non-therapeutic stimuli can be interlaced in between therapeutic stimuli in case of a device configured to provide therapeutic stimulation. The latter approach has the advantage of potentially achieving higher bandwidths. The non-therapeutic signals refer to signals that have sufficiently low amplitude that cannot evoke physiological responses. Further, the non-therapeutic signals need not be restricted to pulses.

As an illustrative example, neurostimulation therapy delivers pulses of mild electrical current to the spinal cord or peripheral nerves to relieve neuro related pain when medication fails to provide adequate relief (or causes intolerable effects). The information can be encoded using such pulses of mild electrical current.

In a still further embodiment, the encoding means and the decoding means is configured to use one of pulse width coding scheme or pulse time coding scheme. These coding schemes allow suitable encoding of the information into the stimulation pulses. Other coding schemes can be applied for the same purpose.

In a still further embodiment, the first implant device and the second implant device is an electro stimulator device and the encoding means and the decoding means is configured to use a pulse time coding scheme. The timing of the electro-stimulation pulses can be modulated to represent information. The pulse time coding scheme has the advantage that it does not affect (i.e. within limits) the therapeutic working of the first implant device and the second implant device.

As a further illustrative example, two deep brain stimulator devices A and B are implanted within the body of the subject. The implant A may need to perform a measurement of the electro physiological activity at the different electrodes addressed by the implant A. This may have to be done in order to detect the optimum position for providing the electrical stimuli. In order to perform proper measurement, interference by the electrical stimuli from the implant B has to be avoided. The reason being that the electrical stimuli from the implant B may contaminate the tiny electro physiological signals that the implant A tries to pick up. In such a scenario, the implant A can send information to the implant B using pulse-timing encoding of the therapeutic stimuli. The information can contain a request for a 'pause' in stimulation by the implant B. The implant B responds with confirmation. This confirmation information can be encoded again in pulse-timings of the stimuli transmitted by the implant B and the implant B can put the stimulation on hold. After receiving the confirmation information, the implant A can commence the measurement of the signals (i.e. signals related to the electro physiological activity at the different electrodes addressed by the implant A). After recording the requested information, the implant A can transmit to the implant B that stimulation can be re-started.

As a further illustrative example, two cortical devices namely implant A and implant B are implanted within the body of the subject. The implant A is a stimulator and needs to receive information of evoked responses (e.g. response-amplitude and response-delay) to its stimuli as measured by the implant B, the implant B being a sensor. In such a scenario, the implant A can send a request to the implant B for measurement of an evoked response. This request can be encoded in pulse-timing of its therapeutic pulses. The implant B can send back a confirmation using sub-therapeutic pulses (i.e. low amplitude). Timing information can be provided by the implant A to the implant B to align the measurement. After measurement of the evoked response, specific parameters and/or the measured signal characteristics can be transmitted by the implant B to the implant A using, for example, pulse-time modulation.

As a still further illustrative example, two stimulator devices namely implant A and implant B are implanted within the body of the subject. The implant A can provide continuous stimulation and implant B can provide stimulation on demand. The implant A can control the timing of the stimulation provided by the implant B by sending appropriate command signals. The command signals and the stimulation parameters can be encoded in the therapeutic stimulation pulses. The implant B can pick up these signals, decode them and arrange for the proper on-demand stimulation. The implant B may confirm receipt of the request by the implant A by sending sub-therapeutic amplitude signals carrying this information.

As a further illustrative example, the deep brain simulator devices can stimulate the body tissue using a nominal frequency, e.g. 130 Hz i.e., an inter-pulse duration of 8 ms. Information can be encoded by using pulse-time modulation scheme. One bit can be encoded by sending a pulse at −0.5 ms or +0.5 ms from the nominal timing. This scheme can be easily extended to encode more bits.

As a further embodiment, the electro stimulation device addresses an array of stimulation electrodes. A first group of stimulation electrodes is used for the delivery of therapeutic electrical pulses at a repetition frequency of 130 Hz. Information may be encoded by interlacing signals in between the therapeutic pulses in the form of a stream of small sub-therapeutic amplitude pulses that are delivered at a relatively high frequency e.g. 2 kHz. In an embodiment, the first group of stimulation electrodes is used to transmit the interlaced information. In another embodiment a second group of electrodes is used to transmit the interlaced information. The first and second group may share a common return-electrode.

In a still further embodiment, the first implant device and the second implant device is an electro stimulator device implanted in the skull and the encoding means is configured to employ a channel for stimulation pulses and encode the information into the stimulation pulses. The conductivity of the skull is much lower than the conductivity of the scalp and the conductivity of the brain tissue e.g., a factor of 25. This can be advantageously used to from a communication channel between two or more deep brain stimulators implanted in the skull if each stimulator has an electrode that comes in good contact with the scalp. The skull can act as the isolation layer in the two-way communication channel. Also, non-therapeutic stimuli can be interlaced in between therapeutic stimuli in case of a device configured to provide therapeutic stimulation. The latter approach has the advantage of potentially achieving higher bandwidths. The non-therapeutic signals refer to signals that have sufficiently low amplitude that cannot evoke physiological responses. Further, the non-therapeutic signals need not be restricted to pulses.

In a still further embodiment, the first implant device comprises at least three electrodes, a first transmit electrode configured to transmit stimulation pulses, a second electrode and a third electrode configured as return electrodes. The position of the second electrode and the third electrode can be switched to produce one or more electric field distributions. The second implant device can be configured to detect the transmitted stimulation pulses.

The advantage of this embodiment is that by switching the return electrodes provided in the first implant device (second electrode alone, third electrode alone or second and third electrodes together) different electrical field distributions can be created and can be used for encoding information.

In a still further embodiment, the first implant device is configured to communicate with an external device using volume conduction of electrical signals as a means of communication. This can be e.g. a controller-unit.

In a second aspect of the present subject matter, a method for communicating information between at least two medical devices implanted within the body of a subject using volume conduction of electrical signals as a means of communication is disclosed. The method comprises:

employing a channel as a transmission medium for stimulation pulses and encoding the information into the stimulation pulses;

transmitting the encoded stimulation pulses using at least two transmit electrodes provided in a first implant device;

receiving the transmitted encoded stimulation pulses using at least two receive electrodes provided in a second implant device; and decoding the information encoded into the stimulation pulses.

The at least two receive electrodes can also be used for transmission and reception and not only for transmission or reception (however not simultaneously). The channel acts as a carrier to transport the signal from the first implant device to the second implant device. The channel is the medium to get the encoded signals across.

BRIEF DESCRIPTION OF THE DRAWINGS

These and other aspects, features and advantages will be further explained by the following description, by way of example only, with reference to the accompanying drawings, in which same reference numerals indicate same or similar parts, and in which.

DETAILED DESCRIPTION OF THE EMBODIMENTS

Figure 1A:
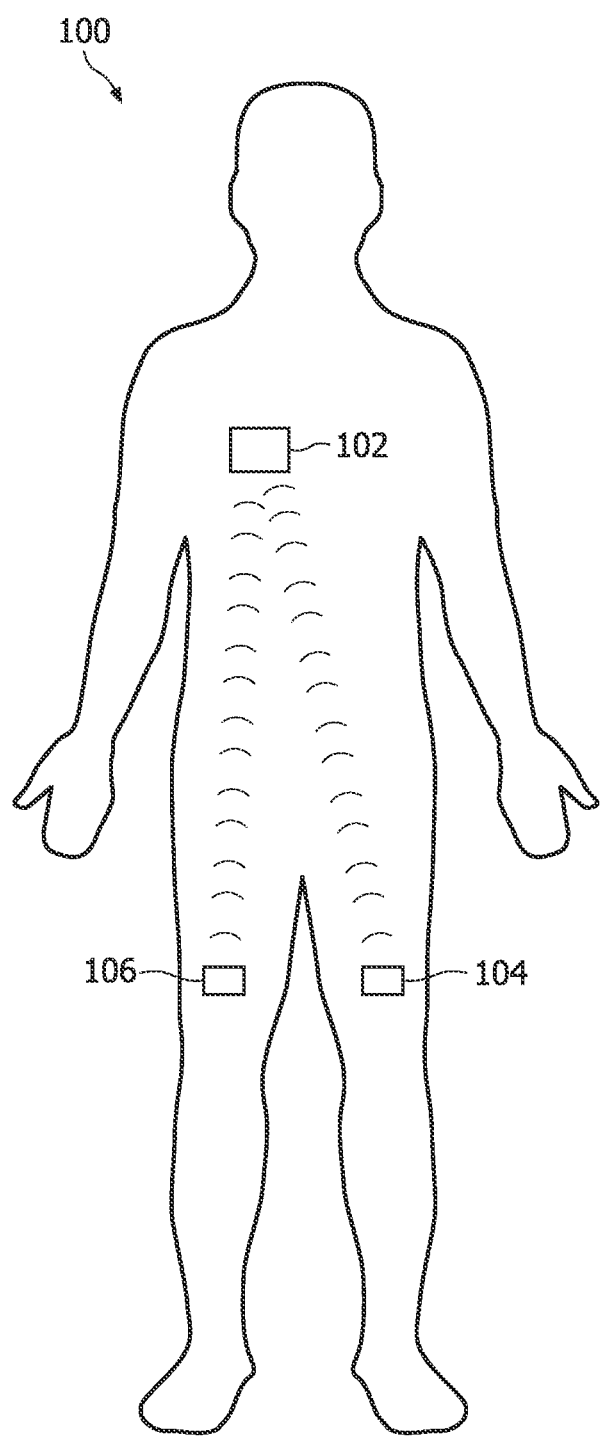
FIG. 1a schematically illustrates a subject with multiple implant devices implanted at various locations in his or her body.

Referring now to FIG. 1a, a subject 100 with multiple implantable devices 102,104,106 implanted at various locations in his (or her) body are shown. The term subject here means a member of the animal kingdom including human beings.

The implanted devices 102,104 and 106 can be multiple instances of the same device, allowing local variations in a parameter to be measured and/or various actions to be performed locally. Alternatively, the implanted devices 102,104, 106 might be different devices.

Figure 1B:
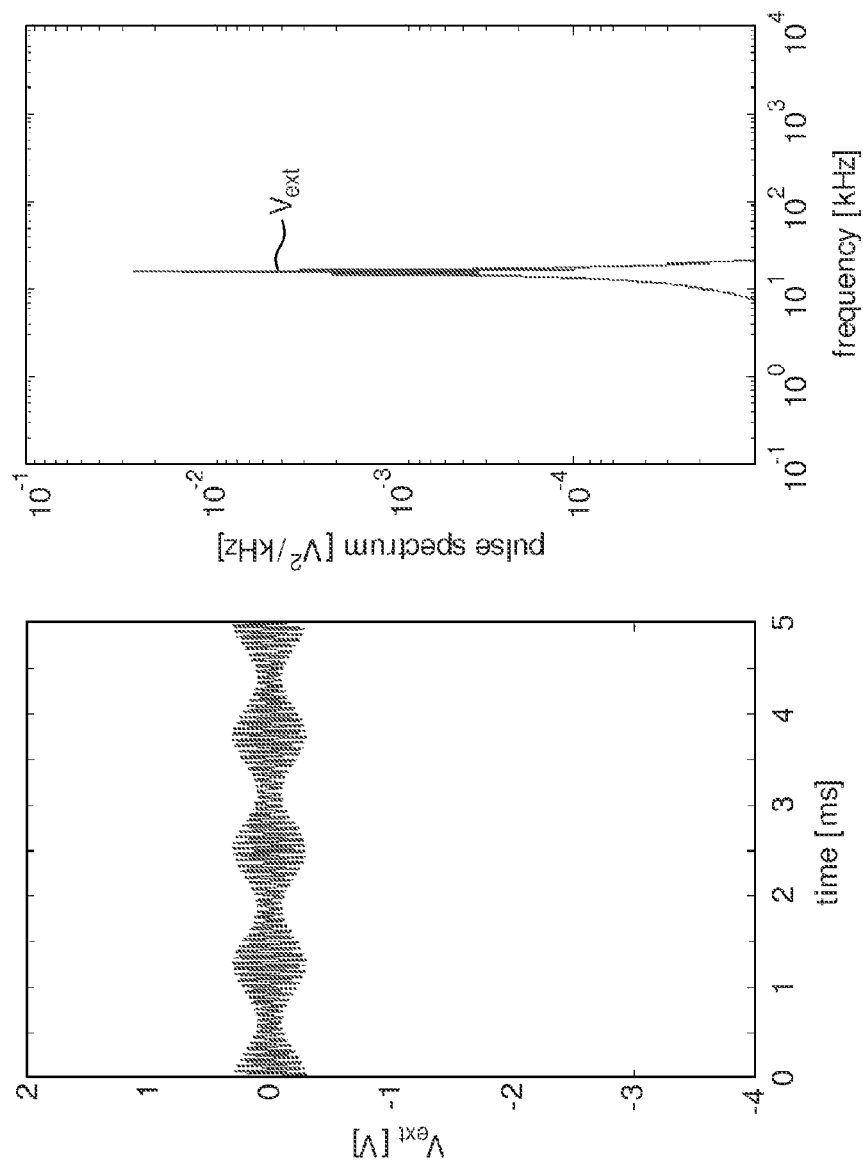
FIG. 1b schematically illustrates an exemplary amplitude modulated carrier signal.
Figure 1C:
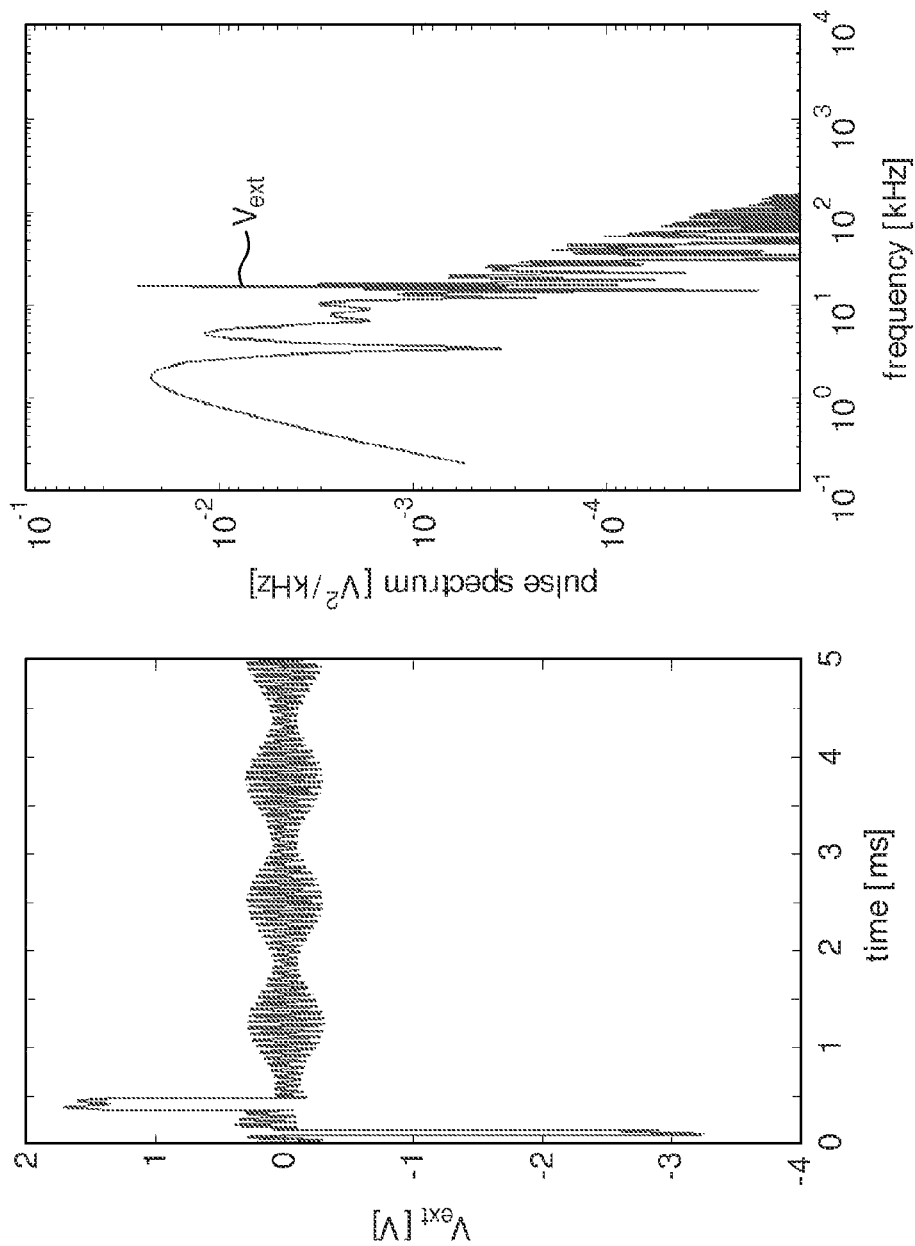
FIG. 1c schematically illustrates an exemplary amplitude modulated carrier signal in the presence of therapeutic stimuli.

Patent document WO2007/028035 discloses a solution for data communication between the implantable devices using quasi-electrostatic coupling between receive and transmit units. The data is transmitted using a carrier signal having a carrier frequency typically in the range of 10-100 KHz. Data is encoded using known modulation techniques e.g. amplitude modulation, frequency modulation or phase modulation of the carrier signal. FIG. 1b schematically shows an exemplary amplitude modulated carrier signal. In the presence of therapeutic electrical stimulation pulses, the high amplitude of the therapeutic stimuli may contaminate the data signal (Cf. FIG. 1c). A higher amplitude data signal could compensate for this but may lead to unwanted and uncontrolled excitation of nervous or muscular tissue. In addition, the demodulation of the data in the presence of therapeutic electrical stimulation pulses may require more complex electronics, increases the bit error rate (BER) and might call for redundant data transmission to enable error correction after encoding.

The solution disclosed in WO2007/028035 may not be well suited for electro-stimulation devices as the stimuli can contaminate the data signals. This can result in unreliable data transmission. Further, the data signal generation may require additional electronics. Dedicated signal generation circuits may be needed to generate the data carrying signal and dedicated transmit/receive electrode pairs may be needed to transmit and receive the data signals.

Figure 2A:
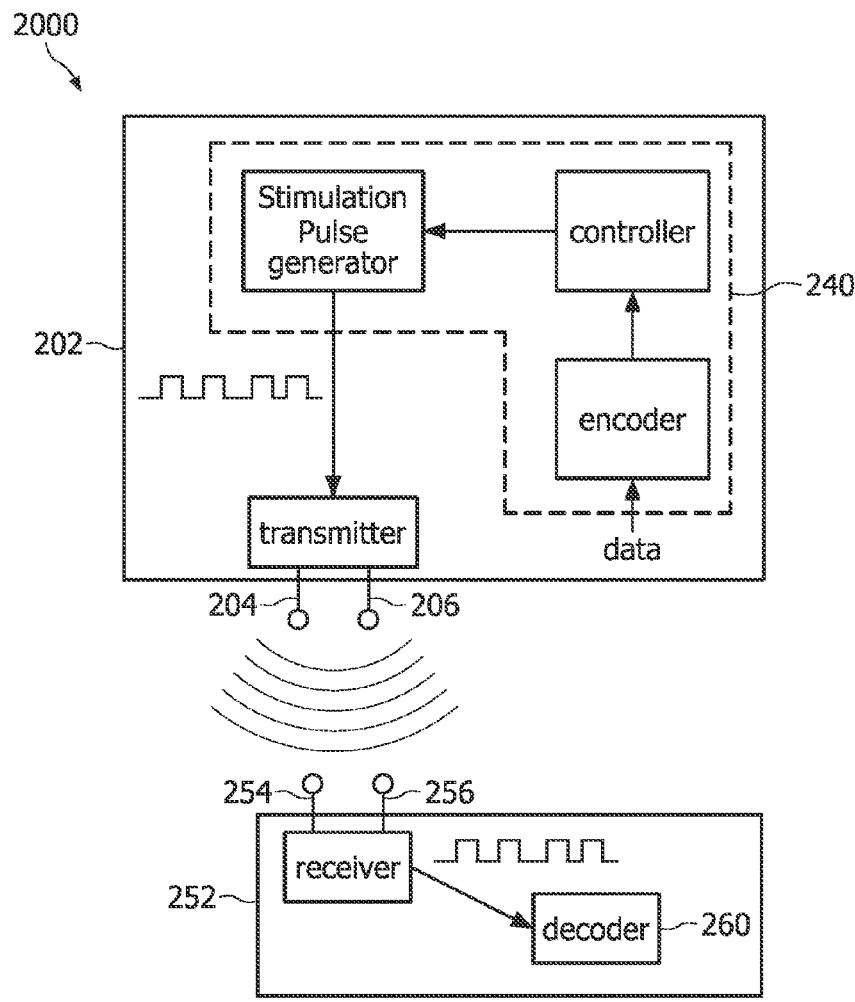
FIG. 2a schematically illustrates an exemplary system for communicating information between two medical devices implanted within the body of the subject according to an embodiment of the present subject matter.
Figure 2B:
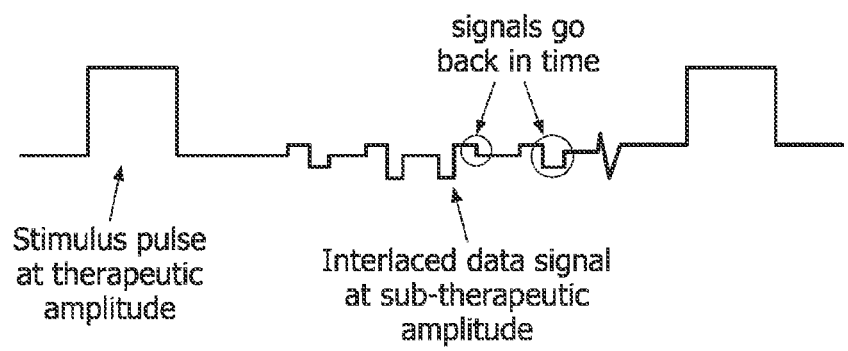
FIG. 2b schematically illustrates an exemplary waveform showing interlaced sub-therapeutic pulses.

Referring now to FIG. 2, the disclosed system 2000 for communicating information between devices implanted within the body of the subject 100 comprises:

1. a first implant device 202 having transmit electrodes 204 and 206
2. a second implant device 252 (or an external device in physical contact with the body) having receive electrodes 254 and 256
3. an encoding means 240
4. a decoding means 260

The first implant device 202 and the second implant device 252 can be located anywhere in the body of the subject provided it is suitably sized, shaped and configured to operate without disrupting a desirable physiological function.

The first implant device 202 and the second implant device 252 can include any electronic, electromechanical or mechanical device that can enter the body of the subject 100 via implantation or ingestion and perform some activity with diagnostic and/or therapeutic significance while inside the body. Further, the first implant device 202 and the second implant device 252 are not physically connected (i.e. they are not wired).

As an illustrative example, the first implant device 202 and the second implant device 252 may be located inside or outside vital organs such as heart, brain, stomach or near surgical sites or wound locations or near a tumor site or within the abdominal cavity or near joints. The first implant device 202 and the second implant device 252 can be employed for cardiovascular applications e.g. pacing applications, cardiac resynchronization therapy applications.

The first implant device 202 is equipped with two transmit electrodes 204 and 206 for transmitting stimulation pulses. Among the two transmit electrodes 204 and 206 one of them (either 204 or 206) can be a common electrode. A voltage difference is applied between the transmit electrodes 204 and 206. An electric field is generated in the body of the subject. The stimulation pulses (i.e. electrical) are transmitted via the generated electric field using volume conduction through the body (e.g. human, animal).

The term volume conduction means transmission of electrical signals (e.g. for data communication) by wireless passage of current through a conductive medium such as living biological tissues.

The transmit electrodes 204 and 206 transmit stimulation pulses. The encoding means 240 receives as input i) the stimulation pulses and ii) the information (or data) to be communicated to the second implant device 252.

The encoding means 240 is configured to employ the channel used for transmitting the stimulation pulses and encode the information into stimulation pulses. In order to encode the information into the stimulation pulses, the encoding means can make use of any information coding scheme. The channel acts as a carrier to transport the signal from one implant to the other. The channel is the medium to get the encoded signals across.

The disclosed solution is based on the insight that the channel that is used for delivery of electric stimuli to the body can be used as well to transmit information. A few options are: i) modulating the timing of the electro stimulation pulses to represent information ii) adding the signals (Cf. FIG. 2) containing the information in between the stimulation pulses (sub-therapeutic amplitude).

Further, by making use of the stimulation pulse signals, the same circuitry and electrodes present in the first implant device and the second implant device for therapeutic use can be re-used for transmitting the information. Hence, there is no need for any additional electronics/circuits for generation of a data-carrier signal.

The output of the encoding means 240 is the encoded stimulation pulses which are transmitted to the second implant device 252 using the principle of volume conduction through the body of the subject as a means of communication.

The second implant device 252 is equipped with two receive electrodes 254 and 256 configured to receive the transmitted stimulation pulses (the receive electrodes could be used for transmission as well). The receive electrodes 254 and 256 are used for receiving the transmitted stimulation pulses by differentially sensing the electric field generated by the first implant device 202 (i.e. by the transmit electrodes 204 and 206). The received encoded stimulation pulses are input to the decoding means 260. The decoding means 260 decodes the information encoded into the stimulation pulses using an appropriate decoding scheme. The second implant device 252 can also be an external device in physical connection to the body.

The transmit electrode can be operated as a receive electrode and vice-versa enabling two way communication or dedicated electrodes for transmit and receive may be present. In other words, the first implant device and the second implant device are equipped with electrical stimulation and sensing functionality and can operate as trans-receivers (i.e. transmit and receive and vice-versa). Not only the stimulation electronics may be reused, for example for the generation of a data-carrier, the sensing electronics may also be applied as part of the receive chain, for example, to amplify the received data signals.

In an embodiment, the encoding means can be configured to use the timing and/or the shape of the therapeutic stimulation pulses as a means to encode the information. This embodiment can effectively make use of the therapeutic pulses that are already generated.

As an illustrative example, nerves partially loosing their function as a result of disease or trauma are generally stimulated using electrical stimulation pulses. A neurostimulator implant can be used for such purpose. The information can be encoded using such electrical stimulation pulses.

In a further embodiment, the encoding means is configured to use non-therapeutic electrical signals (i.e. pulses) as a means to encode the information. Implant devices that are not configured to provide electrical stimulation can use non-therapeutic signals to encode the information. Also, non-therapeutic stimuli can be interlaced in between therapeutic stimuli in case of a device configured to provide therapeutic stimulation. The latter approach has the advantage of potentially achieving higher bandwidths. The non-therapeutic signals refer to signals that have sufficiently low amplitude that cannot evoke physiological responses. Further, the non-therapeutic signals need not be restricted to pulses.

As an illustrative example, neurostimulation therapy delivers pulses of mild electrical current to the spinal cord or peripheral nerves to relieve neuro related pain when medication fails to provide adequate relief (or causes intolerable effects). The information can be encoded using such pulses of mild electrical current.

The encoding means 240 can use pulse width coding scheme or pulse time coding scheme to encode the information into the electrical stimulation pulses. The decoding means 260 uses an appropriate decoding scheme to decode the information that is encoded into the stimulation pulses.

In general, data encoding and decoding schemes as well as signal modulation schemes generally known in the art can be made use of to encode and decode the information into the stimulation pulses.

Figure 3A:
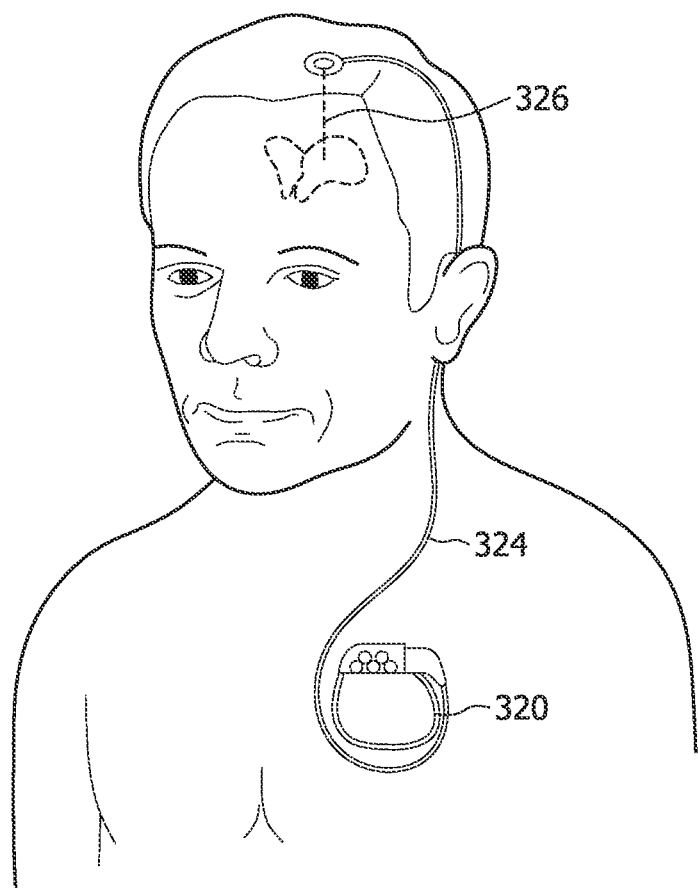
FIG. 3a schematically illustrates a deep brain stimulator system according to an embodiment of the present subject matter.

Referring now to FIG. 3a, a deep brain stimulator system consists of
i) an implanted pulse generator 320 (IPG) that is surgically implanted below the clavicle ii) an extension wire 324 connected to the implanted pulse generator and running through the neck to the skull where it terminates in a connector
iii) a deep brain stimulator probe 326 that is implanted in the brain tissue through a burr-hole in the skull.

As an illustrative example, two deep brain stimulator devices A and B are implanted within the body of the subject. The implant A may need to perform a measurement of the electro physiological activity at the different electrodes addressed by the implant A. This may have to be done in order to detect the optimum position for providing the electrical stimuli. In order to perform proper measurement, interference by the electrical stimuli from the implant B has to be avoided. The reason being that the electrical stimuli from the implant B may contaminate the tiny electro physiological signals that the implant A tries to pick up. In such a scenario, the implant A can send information to the implant B using pulse-timing encoding of the therapeutic stimuli. The information can contain a request for a 'pause' in stimulation by the implant B. The implant B responds with confirmation. This confirmation information can be encoded again in pulse-timings of the stimuli transmitted by the implant B and the implant B can put the stimulation on hold. After receiving the confirmation information, the implant A can commence the measurement of the signals (i.e. signals related to the electro physiological activity at the different electrodes addressed by the implant A). After recording the requested information, the implant A can transmit to the implant B that stimulation can be re-started.

As a further illustrative example, two cortical devices implant A and implant B are implanted with in the body of the subject. The implant A is a stimulator and needs to receive information of evoked responses (e.g. response-amplitude and response-delay) to its stimuli as measured by the implant B, the implant B being a sensor. In such a scenario, the implant A can send a request to the implant B for measurement of an evoked response. This request can be encoded in pulse-timing of its therapeutic pulses. The implant B can send back a confirmation using sub-therapeutic pulses (i.e. low amplitude). Timing information can be provided by the implant A to the implant B to align the measurement. After measurement of the evoked response, specific parameters and/or the measured signal characteristics can be transmitted by the implant B to the implant A using, for example, pulse-time modulation.

As a still further illustrative example, two stimulator devices namely implant A and implant B are implanted with in the body of the subject. The implant A can provide continuous stimulation and implant B can provide stimulation on demand. The implant A can control the timing of the stimulation provided by the implant B by sending appropriate command signals. The command signals and the stimulation parameters can be encoded in the therapeutic stimulation pulses. The implant B can pick up these signals, decode them and arrange for the proper on-demand stimulation. The implant B may confirm receipt of the request by the implant A by sending sub-therapeutic amplitude signals carrying this information.

As a further illustrative example, the deep brain simulator devices (i.e. the first implant device 202 and the second implant device 252) can stimulate the body tissue using a nominal frequency e.g. 130 Hz i.e. an inter-pulse duration of 8 ms. Information can be encoded by pulse time coding. One bit can be encoded by sensing a pulse at −0.5 ms or +0.5 ms from the nominal timing. This scheme can be extended to encode more bits. The pulse time modulation coding scheme is illustrated in FIG. 3b.

Figure 3B:
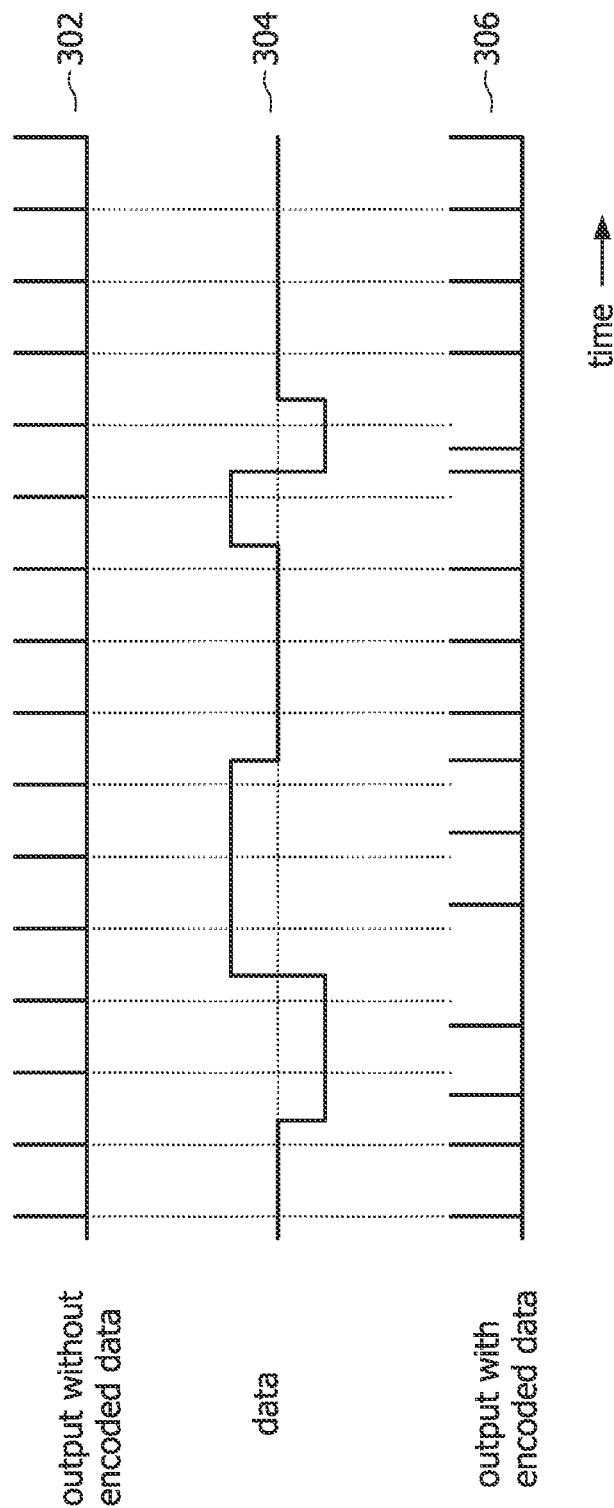
FIG. 3b schematically illustrates pulse timing positions for an exemplary deep brain stimulator device.

Referring now to FIG. 3b, top trace 302 shows nominal pulse timing positions for the deep brain simulator device. The middle trace 304 shows information (or data) to be encoded (low=0; high=1). The bottom trace 306 shows pulse timing modulation to encode the data signal.

It is possible to use various data encoding and decoding schemes as well as signal modulation schemes known in the art to encode the information 280 into the stimulation pulses.

The examples illustrate communication between electrostimulation devices. Such communication can be performed by encoding information in the pulse trains used for therapeutic purposes. The information can be encoded in the timing of the therapeutic pulse signal. Other means for encoding the information into the therapeutic pulse trains are available and can be suitably made use of (e.g. adding signal in the silent phases between pulses).

Figure 4A:
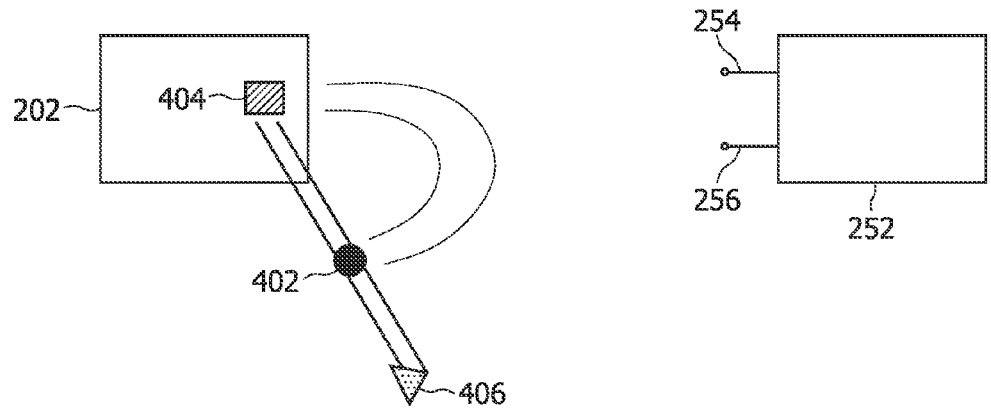
FIG. 4a-4c schematically illustrates further embodiment of the system according to the present subject matter.

Referring now to FIG. 4a, the first implant device 202 comprises at least three electrodes
1. a first transmit electrode 402
2. return electrodes 404 and 406

The second implant device 252 comprises two receive electrodes 254 and 256. The first transmit electrode 402 is configured to transmit stimulation pulses. The return current path can be switched to run via either or both of the return electrodes 404 and 406 (i.e. in the first implant device 202) and thus produce one or more electric field distributions.

Figure 4B:
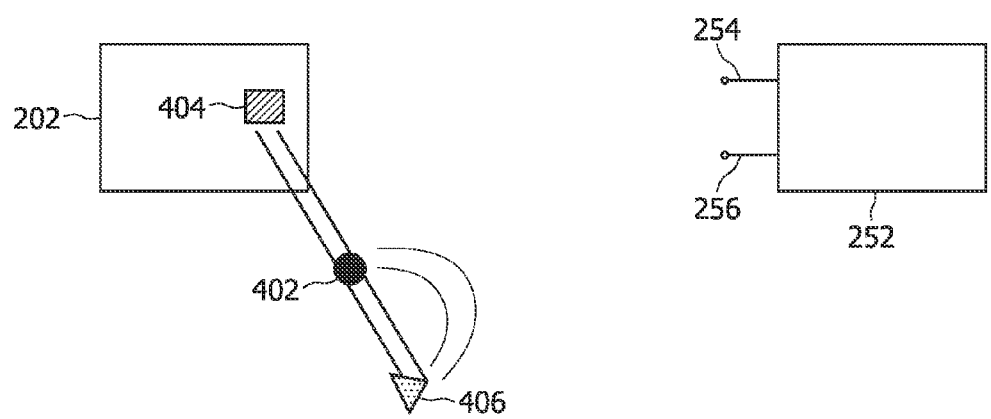
Figure 4C:
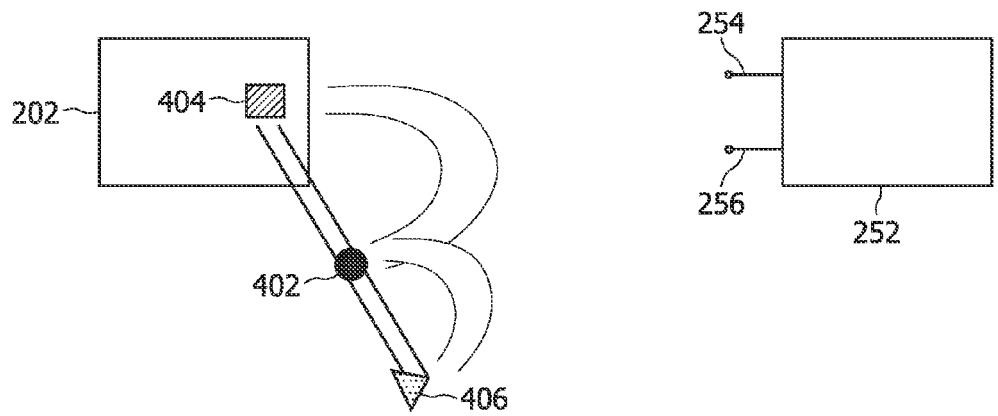

By switching between different position of the return electrode 404 and 406 (indicated by a square and a triangle respectively) different electrical distributions can be set up in the body tissue for a given transmit electrode position 402 (indicated by the circle) as shown in FIGS. 4a, 4b and 4c. The generated electric field distributions can be detected by the receive electrodes 254 and 256 at the second implant device 202. An equivalent effect can be achieved by switching the position of the transmit electrode 402.

The advantage is that by switching the return electrodes (i.e. return electrode 404 alone, return electrode 406 alone or return electrode 404 and return electrode 406 together) different electrical field distributions can be created as shown in FIGS. 4a, 4b and 4c, and can be used for encoding information.

In some embodiments, the first implant device can be configured to communicate with an external device using volume conduction of electrical signals as a means of communication, the external device being in physical contact with the human body.

Figure 5:
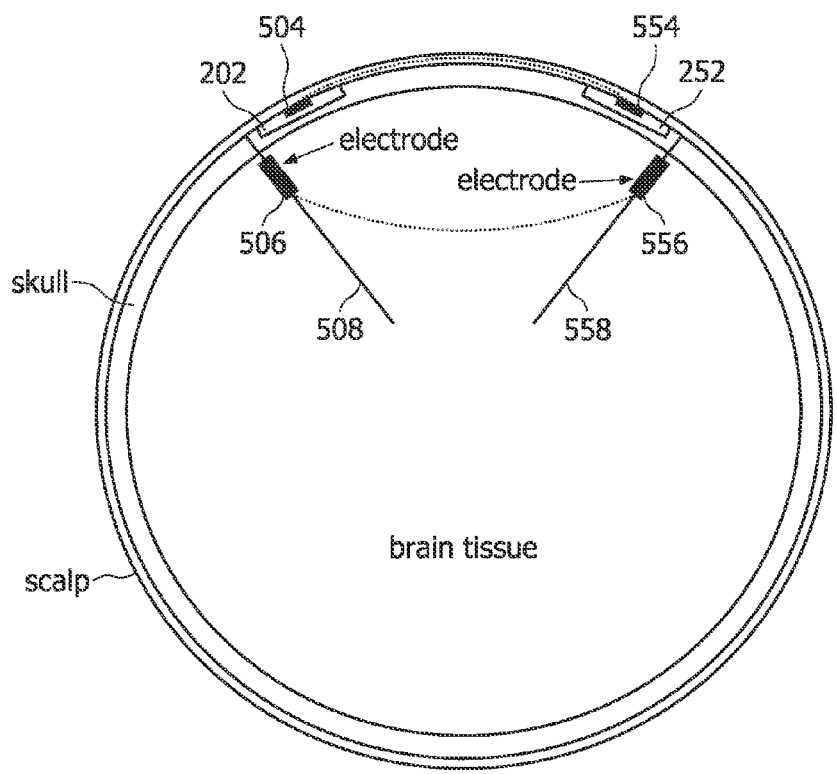
FIG. 5 schematically illustrates a still further embodiment of the system according to the present subject matter wherein an electro stimulator device is implanted in the skull.

Referring now to FIG. 5, the first implant device 202 and the second implant device 252 are implanted in the skull. The first implant device 202 comprises
i) a scalp electrode 504 in contact with the scalp
ii) an electrode 506 on the probe 508, wherein the probe 508 is connected to the first implant device 202, (the connection here implies that the electrode 506 is also electrically connected to the electronics of the device 202 and 252)

The second implant device 252 comprises
i) a scalp electrode 554 in contact with the scalp
ii) an electrode 556 on the probe 558, wherein the probe 558 is connected to the second implant device 252 (the connection here implies that the electrode 556 is also electrically connected to the electronics of the device 202 and 252)

The channel for communicating information between the first implant device 202 and the second implant device 252 is formed using the scalp, the skull and the brain tissue. The communication channel is formed by each electrode on the implant in contact with the scalp (i.e. scalp electrode 504 or scalp electrode 554) and either the (large) return electrode on the probe and/or any of the stimulation electrodes, where the return electrode (i.e. return electrode 506 or return electrode 556) is applied to contact the brain tissue.

The current loop that can be formed is indicated by the dashed circle which is as given below:
scalp electrode 504→electrode 506 on the probe 508→brain tissue→electrode 556 on the probe 558→scalp electrode 554→scalp→scalp electrode 504

The current can also flow via scalp and some electrode on the probe, for example the electrode 506, 556 through the first implant device and the second implant device.

The probes may contain a large electrode which is generally referred to as the return electrode as it is usually connected to ground and collects all the current injected into the brain via some other electrodes on the probe, usually at the distal end. However, this ground electrode can also be any other electrode (or group of electrodes) on the probe, simply depending on which electrode is connected to the ground.

Referring to FIG. 5, a current loop is formed which can be used to convey information while in the other embodiments electric fields i.e. potential differences are measured. The latter implies that at least two electrodes are required for sensing the electric field in the brain tissue, while with a current loop approach one electrode in contact with the brain tissue is sufficient (the other makes a connection with the scalp). The (usually smaller) stimulation electrodes at the distal end of the probe are not shown in FIG. 5, but these can also be used instead of the (usually larger) return electrode on the probe to form a current loop between two (or more) implantables.

The current with sub-therapeutic amplitude can be modulated with any modulation scheme known in the art to convey data from the first implant device to the second implant device and vice-versa. The transmitter can be disposed between the scalp electrode 504 and the return electrode 506 on probe 508 (or any other electrode on the probe). The receiver can be disposed between the scalp electrode 554 and the return electrode 556 on probe 558 (or any other electrode on the probe). Both can be transreceivers to enable bidirectional communication (not simultaneously) between the implants.

Further, the probe and the electronics can be contained in one burr-hole or can occupy different positions on the skull.

Furthermore, non-therapeutic pulses can be interlaced between the stimulation pulses. This implies that every time a non-therapeutic pulse is given, the electrode can be disconnected from the first implant device. The electrode of the first implant device in contact with the scalp can be connected to ground which forces the non-therapeutic current to flow via the brain tissue via the second implant device with its electrode connected to the scalp via the skin back to the electrode of the first implant device.

To summarize, the information can be included in the stimulation pulses themselves and/or interlaced with non-therapeutic pulses.

The method for communicating information between at least two medical devices implanted within the body of a subject using volume conduction of electrical signals comprises the following steps:
a step of employing a channel as a transmission medium for stimulation pulses and encoding the information into the stimulation pulses;
a step of transmitting the encoded stimulation pulses using at least two transmit electrodes provided in a first implant device;

a step of receiving the transmitted encoded stimulation pulses using at least two receive electrodes provided in a second implant device; and a step of decoding the information encoded into the stimulation pulses. The at least two transmit electrodes and the at least two receive electrodes can also be used for receiving and transmitting respectively, however, not simultaneously. Further, the channel acts as a carrier to transport the signal from one implant to the other. The channel is the medium to get the encoded signals across.

In general, the prior art of configuring the implantable devices, electrical volume conduction principles, coding schemes, modulation schemes can be consulted to provide example of how to incorporate them into the disclosed system. Such information is known to the art and is not set forth in detail.

In summary, a system for communicating information between at least two medical devices implanted within the body of a subject using volume conduction of electrical signals as a means of communication and wherein one of the implanted medical devices is configured to provide electrical stimulation to the tissue is disclosed. The system comprises a first implant device having at least two transmit electrodes configured to transmit stimulation pulses, an encoding means configured to employ a channel as a transmission medium for stimulation pulses and encoding the information into the stimulation pulses, a second implant device having at least two receive electrodes configured to receive the transmitted stimulation pulses with encoded information, and a decoding means configured to decode the information encoded into the stimulation pulses. The disclosed system provides reliable and efficient communication between implants. The disclosed system can be employed in diagnostic, therapeutic and general monitoring activities in connection with human beings.

Although claims have been formulated in this application to particular combinations of features, it should be understood that the scope of the disclosure of the present subject matter also includes any novel features or any novel combination of features disclosed herein either explicitly or implicitly or any generalization thereof, whether or not is relates to the same subject matter as presently claimed in any claim and whether or not it mitigates any or all of the same technical problems as does the present subject matter.

Further, while the subject matter has been illustrated in detail in the drawings and foregoing description, such illustration and description are to be considered illustrative or exemplary and not restrictive; the subject matter is not limited to the disclosed embodiments. Other variations to the disclosed embodiments can be understood and effected by those skilled in the art of practicing the claimed subject matter, from a study of the drawings, the disclosure and the appended claims. Use of the verb "comprise" and its conjugates does not exclude the presence of elements other than those stated in a claim or in the description. Use of the indefinite article "a" or "an" preceding an element or step does not exclude the presence of a plurality of such elements or steps. The Figures and description are to be regarded as illustrative only and do not limit the subject matter. Any reference sign in the claims should not be construed as limiting the scope.

The invention claimed is:

1. A system for communicating information between at least two medical devices adapted to be implanted within the body of a subject using volume conduction of electric signals as a means or channel of communication, the system comprising:

a first implant device having (i) at least three transmit electrodes that comprise a first transmit electrode configured to transmit stimulation pulses, and a second electrode and a third electrode configured as return electrodes and (ii) an encoder-controller-pulse generator configured to employ a channel as a transmission or communication medium for the stimulation pulses and to encode the information into the stimulation pulses or between the stimulation pulses, wherein the at least three transmit electrodes and the encoder-controller-pulse generator comprise a same circuitry (a) for transmitting the stimulation pulses for therapeutic use and (b) reused for transmitting the information; and a second implant device (i) having at least two receive electrodes configured to receive the transmitted information encoded into the stimulation pulses or between the stimulation pulses and (ii) a decoder configured to decode the information encoded into or between the stimulation pulses, wherein the encoder-controller-pulse generator of the first implant device further comprises a switch for switching a return current path of the at least three transmit electrodes to run via (i) the second electrode alone, (ii) the third electrode alone, and (iii) both the second electrode and the third electrode together to produce different electric field distributions that encode the information, and wherein the at least two receive electrodes of the second implant device are further configured to detect the different electric field distributions encoded with the information.

2. The system as claimed in claim 1, wherein the encoder-controller-pulse generator is further configured to use at least one of (i) a timing of the simulation pulses, (ii) a shape of the simulation pulses, and (iii) both a timing and a shape of the stimulation pulses as a means to encode the information.

3. The system as claimed in claim 1, wherein the encoder-controller-pulse generator is further configured to interlace data signals in between the stimulation pulses as a means to encode the information and wherein the interlaced data signals are smaller in amplitude than the stimulation pulses.

4. The system as claimed in claim 1, wherein the first implant device and the second implant device each comprise an electro stimulator device and each of the encoder-controller-pulse generator and the decoder is configured to use a pulse time coding scheme.

5. The system as claimed in claim 1, wherein the first implant device and the second implant device each comprise an electro stimulator device adapted to be implanted in a skull and the encoder-controller-pulse generator is configured to employ the channel for stimulation pulses and encode the information into the stimulation pulses.

6. The system as claimed in claim 1, wherein the first implant device is further configured to communicate with an external device using volume conduction or electrical signals as a means of communication.

7. A method for communicating information between at least two medical devices adapted to be implanted within the body of a subject using volume conduction of electrical signals as a means or channel of communication, the method comprising:

employing, via a first implant device, a channel as a transmission or communicating medium for stimulation pulses and encoding the information into or between the stimulation pulses, wherein the first implant device includes (i) at least three transmit electrodes that comprise a first transmit electrode configured to transmit stimulation pulses, and a second electrode and a third electrode configured as return electrodes, and (ii) an encoder-controller-pulse generator, wherein the at least three transmit electrodes and the encoder-controller-pulse generator comprise a same circuitry (a) for transmitting the stimulation pulses for therapeutic use and (b) reused for transmitting the information;

transmitting (i) the stimulation pulses and (ii) the information using the at least three transmit electrodes provided in the first implant device;

receiving, via a second implant device, the transmitted information encoded into or between the stimulation pulses using at least two receive electrodes provided in the second implant device; and decoding the information encoded into or between the stimulation pulses, wherein the encoder-controller-pulse generator of the first implant device further comprises a switch for switching a return current path of the at least three transmit electrodes to run via (i) the second electrode alone, (ii) the third electrode alone, and (iii) both the second electrode and the third electrode together to produce different electric field distributions that encode the information, and wherein the at least two receive electrodes of the second implant device are further configured to detect the different electric field distributions encoded with the information.

* * * * *